(12) United States Patent
Brown et al.

(10) Patent No.: US 7,955,284 B2
(45) Date of Patent: Jun. 7, 2011

(54) CAST PROTECTOR WITHOUT AN INFLEXIBLE SEALING RING

(75) Inventors: Ivan E. Brown, Spirit Lake, IA (US);
Teryle L. Kounkel, Spirit Lake, IA (US)

(73) Assignee: Brown Medical Industires, Sprint Lake, IA (US)

(*) Notice: Subject to any disclaimer, the term of this patent is extended or adjusted under 35 U.S.C. 154(b) by 0 days.

(21) Appl. No.: 12/776,522

(22) Filed: May 10, 2010

(65) Prior Publication Data

US 2010/0249681 A1    Sep. 30, 2010

Related U.S. Application Data

(63) Continuation-in-part of application No. 12/127,316, filed on May 27, 2008, now abandoned.

(51) Int. Cl.
*A61F 5/00* (2006.01)
*A41D 13/015* (2006.01)
(52) U.S. Cl. .................................. 602/3; 2/455
(58) Field of Classification Search ............... 602/3, 20,
602/23; 128/846, 849, 856; 2/16, 22, 26;
119/14.23, 814, 816, 838, 850; 220/495.06,
220/359.1, 359.2, 62.21; 383/26–29, 59–60,
383/220
See application file for complete search history.

(56) References Cited

U.S. PATENT DOCUMENTS

| | | | | | |
|---|---|---|---|---|---|
| 4,346,699 | A | * | 8/1982 | Little et al. | 602/3 |
| 4,530,350 | A | * | 7/1985 | Brown et al. | 602/3 |
| 4,639,945 | A | | 2/1987 | Betz | |
| 4,986,265 | A | * | 1/1991 | Caponi | 602/3 |
| 5,643,183 | A | * | 7/1997 | Hill | 602/3 |
| 6,345,621 | B1 | * | 2/2002 | Chandler et al. | 128/849 |
| 6,916,301 | B1 | * | 7/2005 | Clare | 602/3 |
| 2004/0133144 | A1 | * | 7/2004 | Crichton | 602/62 |
| 2004/0199974 | A1 | * | 10/2004 | Fancher | 2/59 |

FOREIGN PATENT DOCUMENTS

GB    2 287 194 A    9/1995

OTHER PUBLICATIONS

Limbo, "The Waterproof Protectors", Catalogue, dated at least as early as Apr. 30, 1997 (7 pages).
Limbo, "Waterproof Protectors for Showers & Baths (outcast) Weather Protectors for Outdoors", Catalogue, dated at least as early as May 2002 (7 pages).

* cited by examiner

*Primary Examiner* — Patricia M Bianco
*Assistant Examiner* — Tarla R Patel
(74) *Attorney, Agent, or Firm* — McKee, Voorhees & Sease, P.L.C.

(57) ABSTRACT

Cast and bandage protector that avoids use of a separate sealing ring and therefore can be folded over upon itself, has suitability for convenient packaging and at the same time still provides an effective waterproof sealing arrangement.

6 Claims, 5 Drawing Sheets

CAST PROTECTOR WITHOUT AN INFLEXIBLE SEALING RING

CROSS-REFERENCE TO RELATED APPLICATIONS

This application is a Continuation-in-Part of co-pending, commonly assigned, U.S. Ser. No. 12/127,316 filed May 27, 2008, herein incorporated by reference in its entirety.

FIELD OF THE INVENTION

The invention relates to a cast and bandage protector, for use during showers and baths.

BACKGROUND OF THE INVENTION

Casts have been used for well over a hundred years to protect set, broken bones. There are two basis types of casts: plaster of paris and more recently, fiberglass. Although more expensive, fiberglass has certain advantages over plaster, such as lighter in weight, generally longer wearing and often more durable.

Regardless of whether a cast is plaster or fiberglass, they typically have cotton padding in their interior facing the patient's skin surface in order to protect the skin and underlying bones from direct contact or pressure caused by the cast. It is important that neither the cast nor the cotton padding get wet. For example, the cast must be kept dry when bathing or showering. Although a fiberglass cast is impervious to water damage, if the cotton lining becomes wet it may cause skin irritation and possible skin breakdown. Also, moisture will cause the skin to become itchy, and the warm moisture may increase the susceptibility to infection. As a result of the above issues, flexible elastic sleeves have been developed which are used to enshroud either the fiberglass or plaster cast. These elastic sleeves are generally known and commonly sold.

One such prior art sleeve is represented by U.S. Pat. No. 4,639,945 to Betz issued Feb. 3, 1987. Betz provides an elongated flexible plastic sleeve that uses a gasket-like arrangement formed within a surrounding sealing ring. The problem, however, with such sealing ring gasket configurations is that the ring is usually made of semi-rigid waterproof material, which both increases manufacturing expense and prohibits neat and snug folding within a compact package.

This latter point can be significant since store shelf packaging space is important in getting medical device dispensing stores to shelve a product. Put another way, high manufacturing expense and bulky packaging will prevent general store acceptance for shelf display.

Yet another problem with cast protectors for consumer acceptance is that the sleeve must be configured such that it can be easily put on and taken off, and the sleeve must be able to accommodate casts for the arm, for example, that are just simply forearm casts or for the entire arm that need to accommodate the possibility of a 90° bend, for example, at the elbow. This similar situation exists for the leg, ankle and knee. That is to say that one cast protector needs to be available for the entirety of the arm, whether only a forearm cast or a complete arm cast; and similarly one cast protector size needs to be available for the leg in this same way. The number of variations that need to be manufactured can therefore be lessened, even further decreasing manufacturing expense.

Generally, in order to provide patient movement, the tubular material from which a cast protector is made, must be flexible. However, integrity must not be sacrificed for flexibility, since the protector in combination with the opening seal, must protect against entry of moisture. This can be difficult, since the opening seal or diaphragm must be a highly stretchable diaphragm material to allow it to be pulled over casts of a wide variety of diameters. As a result, the diaphragm must be more stretchable, than the flexible cast cover. Such a difference in stretch properties often results in a tear at the point of sealing of the diaphragm and cast cover.

This invention has as one object the making of a cast cover which has a diaphragm that stretches easily over a cast without tearing away at the attachment point to the actual cast cover.

It is another object of the present invention to provide a waterproof shield or sleeve for bandages or casts that can easily be applied and effectively seal the limb in order to prevent water accessing the cast or bandage, during, for example, bathing or showering.

Still another object of the present invention is to provide the above advantages and objectives with a system which is economical to make, and which eliminates the high expense of a separate sealing ring.

A yet further object of the present invention is to provide the above advantages with a cast and bandage protector which can be folded over upon itself for easy, efficient packaging, and conserved shelf space.

An even further objective of the present invention is to provide a cast protector which is a flexible sleeve design to allow easy pull on and take off and which has sufficient flexibility, i.e., a widened area to accommodate up to a 90° bends at covered joints, such as elbows, ankles and knees to allow freedom of movement inside the cast cover.

The foregoing and other objects and advantages of this invention will become apparent to those skilled in the art upon reading the description of a preferred embodiment which follows in conjunction with the below described drawings.

BRIEF SUMMARY OF THE INVENTION

Cast and bandage protector that avoids use of a separate non-flexible sealing ring and therefore can be folded over upon itself, has suitability for convenient packaging, and at the same time still provides an effective waterproof sealing arrangement, with a stretchable diaphragm that will not under normal use tear away from a flexible, non-stretch cast cover.

DETAILED DESCRIPTION OF THE PREFERRED EMBODIMENT

Figure 1:
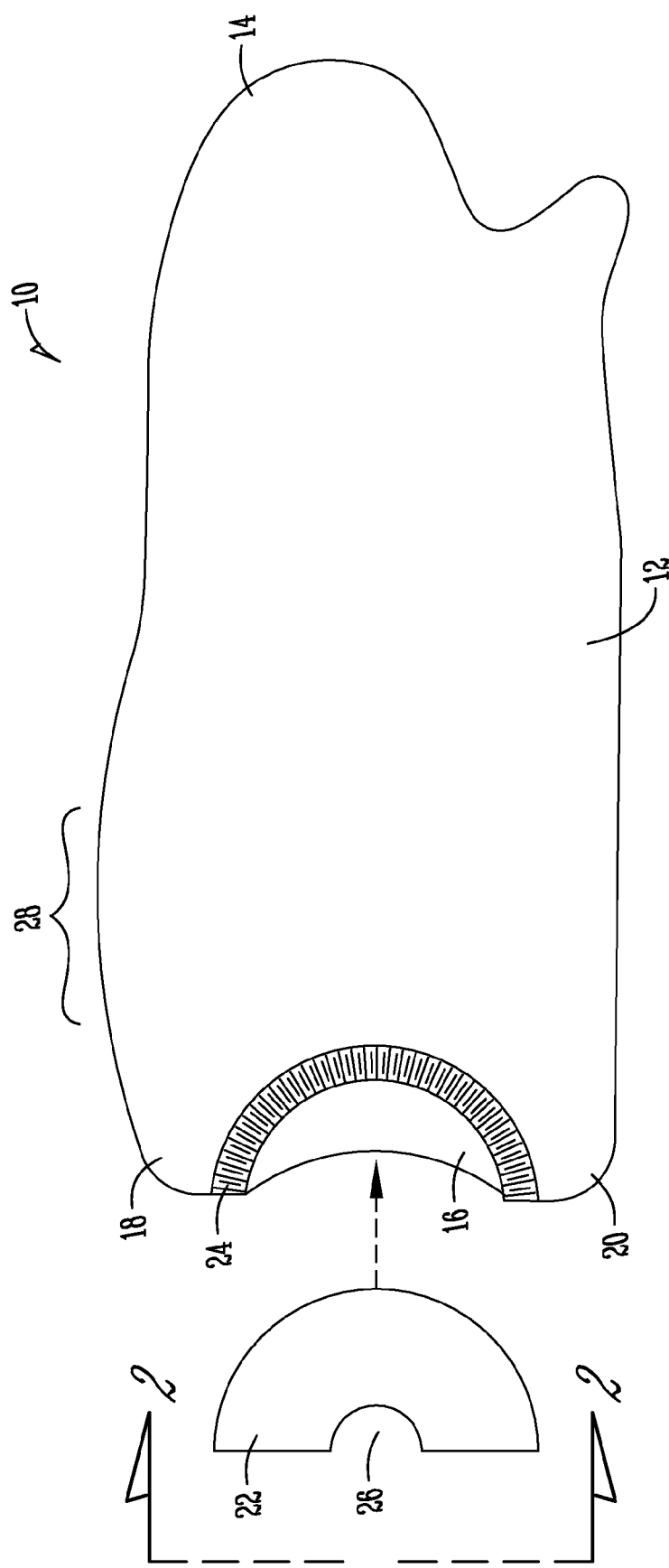
FIG. 1 is a perspective view of a cast protector of the present invention.
Figure 2:
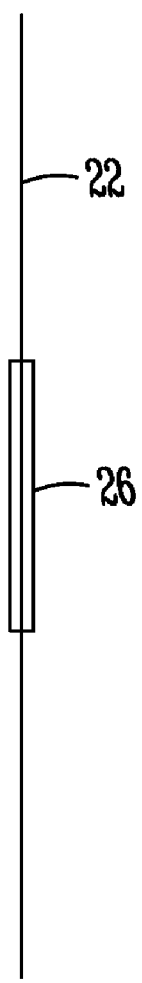
FIG. 2 is an end view of the diaphragm end of the cast protector along line 2-2 of FIG. 1.

FIG. 1 shows a perspective view of the cast with a bandage protector 10 and in this particular instance for use over the arm of the patient. Cast protector 10 is comprised of a flexible waterproof sleeve 12 composed at one end, i.e., hand end 14 of a mitten-like configuration and having an open end in a generally C-configuration 16 at end 14. It is generally made of a flexible, but not particularly stretchable material in order to maximize integrity. Adjacent laterally to the open end 16 are two tab areas 18 and 20 which can be pulled conveniently by grasping with the hand in order to pull the cast protector on over a limb. The diaphragm 22 is stretchable, usually to several times its normal size, has a memory and is adhesively sealed along seal line 24 of flexible sleeve 12. A suitable adhesive which is capable of adhering the elastic diaphragm 22 to the flexible sleeve 24 can be used. Suitable adhesives which form a sealing and secure adhesive moisture impermeable seal include cyanoacrylates. Stretchable diaphragm 22 has an opening 26 that can be stretched many times its natural shape, enough to insert an arm and then when the arm is removed, its memory returns it to its original shape. Diaphragm 22 can be made from either natural or synthetic rubber as long as it has the important stretch characteristics. One synthetic rubber that works is isoprene and blended polyisoprenes. Adjacent tab 18 is a widened area often referred to as a "bump out" 28 (or widened area 28) that allows the same cast protector to be used for only forearm casts or also for casts that go around the elbow at 90° (see FIG. 3). Similar bump out or widened area 28 configuration allows for leg casts as illustrated in FIG. 4.

The flexible sleeve can be made from any polymeric plastic material, usually transparent since user's like to see through it. Flexible sleeves can be made from polymeric, poly vinyl chloride, polyurethane or other alpha olefin from polymers, i.e., polyethylene, polypropylene, etc.

Figure 5:
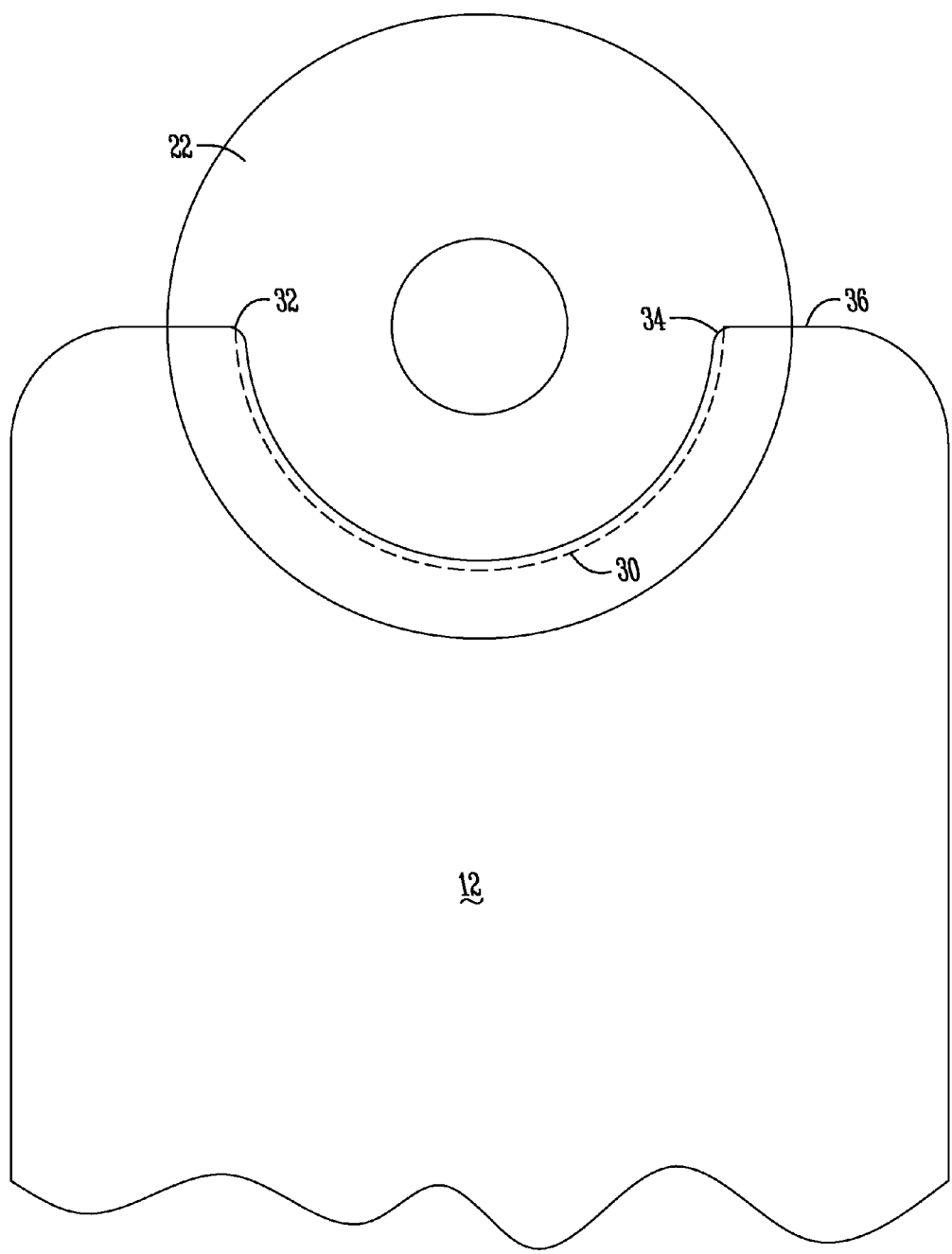
FIG. 5 is an exploded view of the cut line and corner forming the seal between the diaphragm and the cast cover.

FIG. 5 illustrates an extremely important feature of the present invention. Dotted line 30 shows the old cut line in first versions of the cast protector. As can be seen at corner 32, it used a 90° corner, so that it and the diaphragm 22 exactly coincided at the bonding corner. Trial and error allowed for the discovery that if the cut has a "released radius cut" as shown at 34, when the diaphragm is stretched, the pulling force is exerted down from the corner 32 of the cast cover, and as a result the tendency of the cast cover to tear away is substantially diminished. As used herein, released radius means that the circumferential cut of the open end of the flexible fabric does not go all the way to the outside perimeter 36 normal corner edge 32 of the material, but stops short of it to provide a "released radius cut out", having a sort of step as illustrated.

Figure 3:
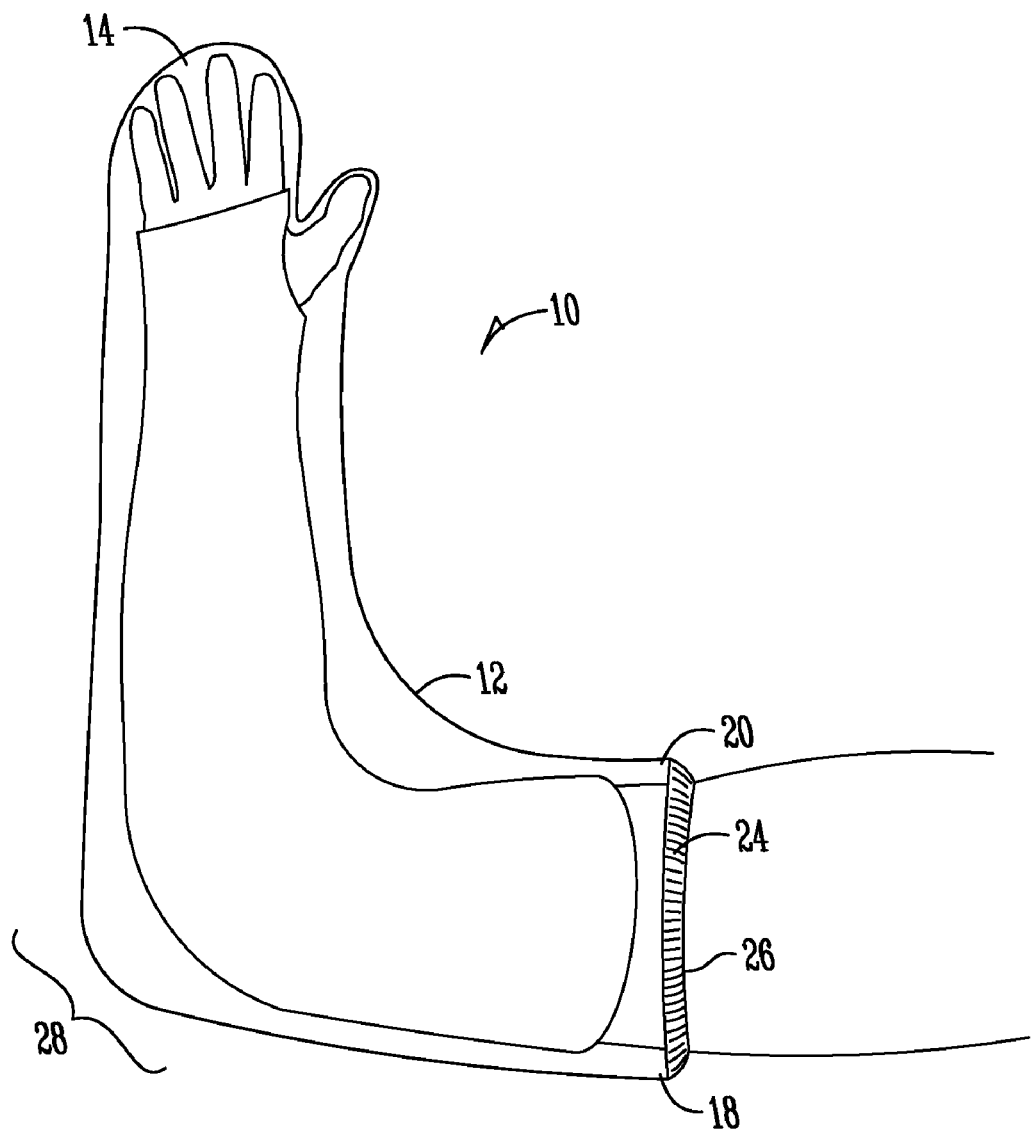
FIG. 3 illustrates a human limb schematically and in perspective to demonstrate the use of the protector on an arm.
Figure 4:
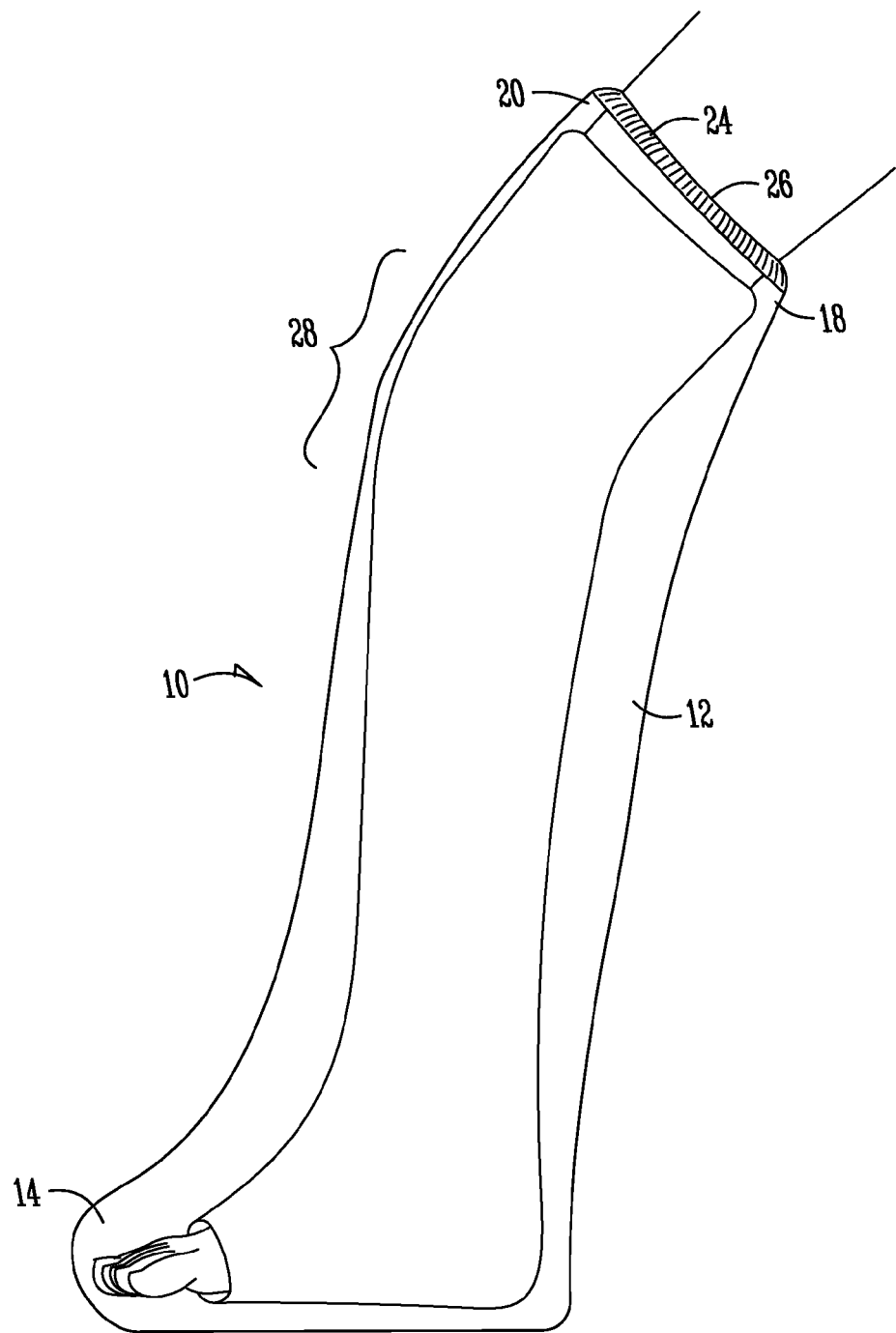
FIG. 4 is a view similar to FIG. 3 of the cast protector over a leg.

In using the cast and bandage protector as illustrated in FIGS. 3 and 4, one grasps tabs 18 and 20, pulls the sleeve over the arm which is inserted through the diaphragm opening 26, so the stretched opening seals against the arm to make the cast and bandage protector impervious to water. The proper seal is therefore achieved around the limb. And, since the diaphragm folds it can be snugly packaged.

While the embodiments of this invention shown and described are fully capable of achieving the objects and advantages desired, it is to be understood that such embodiments have been shown for purposes of illustration only, and not for purposes of limitation with the claims below, providing the meets and bounds of the invention.

What is claimed is:

1. A cast and bandage protector, comprising:
   a flexible sleeve of water proof material closed at one end and open at the other end;
   said open other end having a flexible and stretchable rubber diaphragm of a different material than the bandage protector sealingly and adhesively attached to said flexible sleeve of water proof material;
   said flexible sleeve being configured to provide pull tabs alongside the rubber diaphragm and a widened area to accommodate up to 90° bends at covered joint areas, such as elbows, ankles and knees.

2. The cast and bandage protector of claim 1 wherein the rubber diaphragm has virtually a 100% return memory after stretching.

3. The cast and bandage protector of claim 1 wherein the entire protector including the diaphragm is foldable to provide for small space packaging.

4. The cast and bandage protector of claim 1 wherein the flexible sleeve is made from a polymeric material selected from polyvinyl chloride, polyurethane or other alpha polyolefin polymers.

5. The cast and bandage protector of claim 1 wherein the sealing and adhesive attachment of said diaphragm to said sleeve is with a cyanoacrylate adhesive.

6. The cast protector of claim 1 wherein the cast and bandage protector flexible sleeve has a released radius cut at the location of sealing and adhesive attachment to said flexible and stretchable diaphragm.

* * * * *